US008623853B2

(12) United States Patent
French et al.

(10) Patent No.: US 8,623,853 B2
(45) Date of Patent: Jan. 7, 2014

(54) **TREATMENT OF CANCERS CHARACTERIZED BY CHROMOSOMAL REARRANGEMENT OF THE *NUT* GENE**

(75) Inventors: Christopher French, Boston, MA (US);
Jon Aster, Lexington, MA (US);
Matthias Hofer, Chicago, IL (US);
James Bradner, Cambridge, MA (US)

(73) Assignees: The Brigham and Women's Hospital, Inc., Boston, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 13/055,381

(22) PCT Filed: Jul. 21, 2009

(86) PCT No.: PCT/US2009/051328
§ 371 (c)(1),
(2), (4) Date: May 18, 2011

(87) PCT Pub. No.: WO2010/011700
PCT Pub. Date: Jan. 28, 2010

(65) Prior Publication Data
US 2011/0213012 A1     Sep. 1, 2011

Related U.S. Application Data

(60) Provisional application No. 61/129,839, filed on Jul. 23, 2008.

(51) Int. Cl.
| | |
|---|---|
| *A01N 43/00* | (2006.01) |
| *A01N 43/40* | (2006.01) |
| *A01N 43/38* | (2006.01) |
| *A01N 43/08* | (2006.01) |
| *A01N 37/28* | (2006.01) |
| *A61K 31/33* | (2006.01) |
| *A61K 38/00* | (2006.01) |
| *A61K 38/12* | (2006.01) |
| *A61K 31/44* | (2006.01) |
| *A61K 31/405* | (2006.01) |
| *A61K 31/34* | (2006.01) |
| *A61K 31/205* | (2006.01) |

(52) U.S. Cl.
USPC ......... 514/183; 514/19.3; 514/19.9; 514/352; 514/415; 514/469; 514/507

(58) Field of Classification Search
USPC ............... 514/183, 575, 576, 19.3, 19.9, 352, 514/415, 469, 507
See application file for complete search history.

(56) References Cited

U.S. PATENT DOCUMENTS

| | | |
|---|---|---|
| 6,495,719 B2 | 12/2002 | Lan-Hargest et al. |
| 6,541,661 B1 | 4/2003 | Delorme et al. |
| 6,638,530 B1 | 10/2003 | Ishibashi et al. |
| 6,673,587 B1 | 1/2004 | Evans et al. |
| 6,897,220 B2 | 5/2005 | Delorme et al. |
| 6,905,669 B2 | 6/2005 | DiMartino |
| 7,057,057 B2 | 6/2006 | Lan-Hargest et al. |
| 7,091,229 B2 | 8/2006 | Georges et al. |
| 7,135,493 B2 | 11/2006 | Urano et al. |
| 7,154,002 B1 | 12/2006 | Bressi et al. |
| 7,169,801 B2 | 1/2007 | Bressi et al. |
| 7,193,105 B2 | 3/2007 | Lan-Hargest et al. |
| 7,205,304 B2 | 4/2007 | Van Emelen et al. |
| 7,214,831 B2 | 5/2007 | Lan-Hargest et al. |
| 7,244,751 B2 | 7/2007 | Lu et al. |
| 7,250,504 B2 | 7/2007 | Grozinger et al. |
| 7,250,514 B1 | 7/2007 | Xiao |
| 7,253,204 B2 | 8/2007 | Delorme et al. |
| RE39,850 E | 9/2007 | Delorme et al. |
| 7,265,154 B2 | 9/2007 | Gottlicher et al. |
| 7,271,195 B2 | 9/2007 | Wash et al. |
| 7,282,608 B2 | 10/2007 | Raeppel et al. |
| 7,288,567 B2 | 10/2007 | Delorme et al. |
| 7,291,492 B2 | 11/2007 | Zelent et al. |
| 7,312,247 B2 | 12/2007 | Lan-Hargest et al. |
| 7,345,043 B2 | 3/2008 | Anandan et al. |
| 7,368,572 B2 | 5/2008 | Sendzik |
| 7,375,137 B2 | 5/2008 | Bacopoulos et al. |
| 7,375,228 B2 | 5/2008 | Bressi et al. |
| 7,381,749 B2 | 6/2008 | Malecha et al. |
| 7,381,825 B2 | 6/2008 | Bressi et al. |
| 2005/0123896 A1 | 6/2005 | Benz |
| 2005/0288282 A1 | 12/2005 | Delorme et al. |
| 2006/0020131 A1 | 1/2006 | Raeppel et al. |
| 2006/0030543 A1 | 2/2006 | Malecha et al. |
| 2006/0030554 A1 | 2/2006 | Malecha et al. |
| 2006/0047123 A1 | 3/2006 | Ahmed et al. |

(Continued)

OTHER PUBLICATIONS

Blumenschein Jr., G.R., et al. Phase II Trial of the histone deacetylase inhibitor vorinostat (Zolinza, suberoylanalide hydroxamic acid, SAHA) in patients with recurrent and/or metastatic head and neck cancer. Invest. New Drugs vol. 26 pp. 81-87. Published online Oct. 25, 2007.*

(Continued)

*Primary Examiner* — Brandon J. Fetterolf
*Assistant Examiner* — George W Kosturko
(74) *Attorney, Agent, or Firm* — Law Office of: Michael A. Sanzo, LLC

(57) ABSTRACT

The present invention is directed, inter alia, to methods of treating NUT midline carcinoma (NMC) by administering compounds that promote increased histone acetylation. The invention also includes assay methods for determining the responsiveness of NMC to specific histone deacetylases and other compounds.

20 Claims, No Drawings

(56) References Cited

U.S. PATENT DOCUMENTS

| | | |
|---|---|---|
| 2006/0052599 A1 | 3/2006 | Ishibashi et al. |
| 2006/0106049 A1 | 5/2006 | Odenike |
| 2006/0148743 A1 | 7/2006 | Jadhav et al. |
| 2006/0167103 A1 | 7/2006 | Bacopoulos et al. |
| 2006/0199829 A1 | 9/2006 | Anandan et al. |
| 2006/0235231 A1 | 10/2006 | Joel et al. |
| 2006/0264415 A1 | 11/2006 | Leit de Moradei et al. |
| 2007/0037869 A1 | 2/2007 | Lan-Hargest et al. |
| 2007/0060614 A1 | 3/2007 | Bacopoulos et al. |
| 2007/0105808 A1 | 5/2007 | MacLeod et al. |
| 2007/0122507 A1 | 5/2007 | Palu et al. |
| 2007/0135424 A1 | 6/2007 | Van Brandt et al. |
| 2007/0135431 A1 | 6/2007 | Smith et al. |
| 2007/0135438 A1 | 6/2007 | Payne et al. |
| 2007/0142393 A1 | 6/2007 | Emelen et al. |
| 2007/0149495 A1 | 6/2007 | Bressi et al. |
| 2007/0213330 A1 | 9/2007 | Delorme et al. |
| 2007/0281934 A1 | 12/2007 | Buggy et al. |
| 2007/0292351 A1 | 12/2007 | Li et al. |
| 2007/0293530 A1 | 12/2007 | Smil et al. |
| 2008/0015190 A1 | 1/2008 | Chakravarty et al. |
| 2008/0015216 A1 | 1/2008 | Belvedere et al. |
| 2008/0033015 A1 | 2/2008 | Belvedere et al. |
| 2008/0039509 A1 | 2/2008 | Lu et al. |
| 2008/0096920 A1 | 4/2008 | Belvedere et al. |
| 2008/0108601 A1 | 5/2008 | Van Emelen et al. |
| 2008/0112889 A1 | 5/2008 | Buggy et al. |
| 2008/0132459 A1 | 6/2008 | Moradei et al. |
| 2008/0132503 A1 | 6/2008 | Moradei et al. |
| 2008/0139535 A1 | 6/2008 | Anandan et al. |
| 2008/0139547 A1 | 6/2008 | Sendzik et al. |
| 2008/0146623 A1 | 6/2008 | Deziel et al. |

OTHER PUBLICATIONS

French, C.A., et al. Oncogene vol. 27. pp. 2237-2242. Published online Oct. 15, 2007.*
Stelow, E.B., et al. Am. J. Surg. Path. vol. 32. pp. 828-834. Published Jun. 2008.*
Fornelli R.A., et al. Otolaryngology—Head and Neck Surgery. vol. 123, pp. 207-210. Published Sep. 2000.*
Ryan, Q.C., et al. Journal of Clinical Oncology vol. 23, pp. 3912-3922. Published 2005.*
Kelly, W.K., et al. Journal of Clinical Oncology vol. 23, pp. 3923-3931. Published 2005.*
Blumenschein, G.R., et al., Invest. New Drugs. vol. 26, pp. 81-87, published online Oct. 27, 2007.*
Marks, P.A., et al. Nature Reviews Cancer vol. 1 pp. 194-202. Published 2001.*
Kubonishi, I., et al. Cancer Research vol. 51 pp. 3327-3328. Published 1991.*
International Search Report for PCT/US2009/051328 filed Jul. 21, 2009.
Written Opinion of the International Searching Authority for PCT/US2009/051328 filed Jul. 21, 2009.
International Preliminary Report on Patentability for PCT/US2009/051328 filed Jul. 21, 2009.
Duvic, et al., "Phase 2 trial of oral vorinostat (suberoylanilide hydroxamic acid, SAHA) for refractory cutaneous T-cell lymphoma (CTCL)," *Blood* 109(1):31-39 (Jan. 2007).
Engleson, et al., "Midline carcinoma with t(15;19) and *BRD4-NUT* fusion oncogene in a 30-year-old female with response to docetaxel radiotherapy," *BMC Cancer* 6:69 (2006).
French, et al., "*BRD4* Bromodomain Gene Rearrangement in Aggressive Carcinoma with Translocation t(15;19)," *Am. J Pathol.* 159(6):1987-1992 (Dec. 2001).
French, et al., "*BRD4-NUT* Fusion Oncogene: A Novel Mechanism in Aggressive Carcinoma," *Cancer Res.* 63(2):304-307 (Jan. 2003).
French, et al., "Midline Carcinoma of Children and Young Adults With *Nut* Rearrangement," *J. Clin. Oncol.* 22(20):4135-4139 (Oct. 2004).
French, et al., "BRD-NUT oncoproteins: a family of closely related nuclear proteins that block epithelial differentiation and maintain the growth of carcinoma cells," *Oncogene* 27(15):2237-2242 (2008).
Kees, et al., "Intrathoracic Carcinoma in an 11 Year-Old Girl Showing a Translocation t(15;19)," *Am. J. Pediatr. Hematol. Oncol.* 13(4):459-464 (1991).
Kuzume, et al., "Establishment and Characterization of a Thymic Carcinoma Cell Line (Ty-82) Carrying t(15;19)(q15;p13) Chromosome," *Int. J Cancer* 50(2):259-264 (1992).
Mertens, et al., "Successful Treatment of a Child With t(15;19)-Positive Tumor," *Pediatr. Blood Cancer* 49(7):1015-1017 (2007).
Minucci, et al., "Histone deacetylase inhibitors and the promise of epigenetic (and more) treatments for cancer," *Nature Reviews Cancer* 6(1):38-51 (Jan. 2006).
Mochizuki, et al., "The Bromodomain Protein Brd4 Stimulates $G_1$ Gene Transcription and Promotes Progression to S Phase," *J Biol. Chem.* 283(14):9040-9048 (Apr. 2008) and supplemental material.
Schwartz, et al., "Differentiation of NUT Midline Carcinoma by Epigenomic Reprogramming," *Cancer Res.* 71(7):2686-2696 (2011).
Stelow, et al., "NUT Rearrangement in Undifferentiated Carcinomas of the Upper Aerodigestive Tract," *Am. J Surg. Pathol.* 32:828-834 (2008).
Thorpe, et al., "Chromosomal localization, gene structure and transcription pattern of the *ORFX* gene, a homologue of the MHC-linked RING3 gene," *Gene* 200(1-2) 177-183 (1997).
Toretsky, et al., "Translocation (11;15;19): a Highly Specific Chromosome Rearrangement Associated With Poorly Differentiated Thymic Carcinoma in Young Patients," *Am. J. Clin. Oncol.* 26(3):300-306 (2003).
Wade, et al., "Histone acetylation: chromatin in action," *Trends Biochem. Sci.* 22:128-132 (1997).
Wolffe, "Histone Deacetylase: A Regulator of Transcription," *Science* 272:371-372 (1996).
Wu, et al., "The Double Bromodomain-containing Chromatin Adaptor Bd4 and Transcriptional Regulation," *J. Biol. Chem.* 282(18):13141-13145 (2007) and supplemental material.
Yang, et al., "Brd4 Recruits P-TEFb to Chromosomes at Late Mitosis to Promote $G_1$ Gene Expression and Cell Cycle Progression," *Mol. Cell. Biol.* 28(3):967-976 (2008).

* cited by examiner

TREATMENT OF CANCERS CHARACTERIZED BY CHROMOSOMAL REARRANGEMENT OF THE *NUT* GENE

CROSS REFERENCE TO RELATED APPLICATIONS

The present application is US national stage of international application PCT/US2009/051328, which had an international filing date of Jul. 21, 2009 and claims the benefit of U.S. provisional application 61/129,839, filed on Jul. 23, 2008, the contents of which is hereby incorporated by reference in its entirety. The PCT application was published in English under PCT Article 21(2) on Jan. 28, 2010.

STATEMENT OF GOVERNMENT FUNDING

This invention was made with Government support under Grant No. IR01CA124633-01-5 awarded by the National Institutes of Health. The U.S. Government therefore has certain rights in the invention.

FIELD OF THE INVENTION

The present invention is concerned with methods of treating patients with cancers in which there has been a chromosomal rearrangement that results in a fusion between the NUT (nuclear protein in testis) gene, and a bromodomain gene (BRD3 or BRD4) or other, as yet uncharacterized fusion partner genes. In particular, it is directed to the treatment of these patients with agents that promote increased histone modification, especially acetylation by histone deacetylase inhibitors.

BACKGROUND

NUT Midline Carcinoma

NUT midline carcinoma, or "NMC," is a rare form of cancer characterized by a chromosomal rearrangement in which a portion of the NUT (nuclear protein in testis) gene on chromosome 15 is fused to a BRD (bromodomain protein) gene or other, as yet unidentified, gene (French, et al., *Cancer Res.* 63(2):304-307 (2003); French, et al., *J. Clin. Oncol.* 22(20):4135-4139 (2004); French, et al., *Oncogene* 27(15): 2237-2242 (Apr. 3, 2007)). NUT fusion genes encode oncoproteins that maintain cells in an undifferentiated state and promote their rapid and uncontrolled growth. The frequent involvement of midline structures in the head, neck, mediastinal, and other midline structures, suggest that NMCs arise from primitive neural crest-derived cells. NMCs are very aggressive clinically, respond poorly to conventional chemotherapy, and are almost uniformly fatal.

BRD4 was originally named MCAP (Mitotic Chromosome-Associated Protein) because it remains bound to chromatin via its two bromodomains during mitosis. It is thought to bind in the region of actively transcribed genes before mitosis, thus providing a kind of cellular memory that ensures re-initiation of transcription from these sites after mitosis is completed. Two recent studies provide evidence that this may indeed be the case (Yang, et al., *Mol. Cell Biol.* 28(3):967-76 (2008); Mochizuki, et al., *J. Biol. Chem.* 283(14):9040-9048 (2008)). The function of BRD3 is less well characterized but, like all proteins in the BRD family, it contains two acetyl-histone-binding bromodomains and an extra terminal domain (Wu, et al., *J. Biol. Chem.* 282(18):13141-13145 (2007); Thorpe, et al., *Gene* 200(1-2):177-183 (1997)). BRD3 is highly homologous to BRD4 and so its involvement in NMC is not unexpected. About two thirds of NMCs result from fusion of NUT to BRD4, and the remaining result from fusion of NUT to BRD3 or other, as yet uncharacterized, gene (French et al., *Oncogene* 27 (15):2237-2242 (Apr. 3, 2007)).

In contrast to BRD proteins, NUT lacks known functional domains, is poorly conserved, and is apparently restricted to mammals. Although NUT normally shuttles between the nucleus and cytoplasm, it remains bound to chromatin when fused to BRD4 or BRD3 (French, et al., *Oncogene* 27(15): 2237-2242 (Apr. 3, 2007)). This suggests that the BRD moiety of the fusion protein serves to tether NUT to chromatin, thus modifying the function of either or both proteins in a way that affects transcription. One important consequence of BRD-NUT expression has been discovered using siRNA to silence the expression of BRD3- or BRD4-NUT in NMC cell lines. It was found that withdrawal of the NUT fusion proteins resulted in irreversible squamous differentiation and arrested growth (French, et al., *Oncogene* 27(15):2237-2242 (Apr. 3, 2007)). These findings suggest that BRD-NUT proteins block differentiation.

Histone Deacetylase Inhibitors

During the last few years, it has become increasingly clear that the acetylation of histones plays a central role in the structure of chromatin and gene regulation. Acetylation reduces the positive charge of histones, thereby relaxing the structure of the nucleosome and facilitating the interaction of transcription factors with DNA. Removal of the acetyl group restores the positive charge, thereby causing the nucleosome to contract and become less accessible to transcription factors (Wade et al., *Trends Biochem. Sci.* 22:128 132 (1997); and Wolffe, *Science* 272:371-372 (1996)).

Histone deacetylases (HDACs) catalyze the removal of acetyl groups from histones and appear to play a particularly important role in regulating gene expression. HDACs are segregated into four functionally related classes based on sequence homology to characterized yeast proteins Inhibition of class I HDACs has been actively pursued as an anticancer strategy due to epigenetic changes that affect gene expression in cancer cells. At least one HDAC inhibitor, vorinostat, has been approved by the FDA for use in certain cancers. Activity has been documented in hematologic malignancies, in particular, cutaneous T-cell lymphoma (Minucci, et al., *Nature Reviews* 6(1):38-51 (2006); Duvic, et al., *Blood* 109(1):31-39 (2007)). Dose-limiting toxicities for this class of drug include fatigue, nausea, lethargy and myelosuppression, in particular thrombocytopenia.

SUMMARY OF THE INVENTION

The present invention is based upon the discovery that cancer cells carrying BRD-NUT chromosomal rearrangements respond to histone deacetylase (HDAC) inhibitors by becoming more differentiated and slowing their rate of growth. Thus, HDAC inhibitors should be effective in treating NUT midline carcinoma, a rare cancer that is characterized by the presence of these rearrangements.

In its first aspect, the invention is directed to a method of treating a patient that has been diagnosed as having a cancer characterized by cells with a chromosomal translocation involving NUT (e.g., BRD4-NUT or BRD3-NUT) or by the presence of bromodomain proteins that exist as translocation partners (or that are fused to proteins critical to transcription) by administering a therapeutically effective amount of a compound that promotes modification, especially increased acetylation, of histones. The most preferred compounds are histone deacetylase (HDAC) inhibitor compounds such as SAHA, FK-228, LBH-589, CRA-024781 (also called PCI- 24781), and MS275, but small interfering RNAs may also be used either alone or in conjunction with HDAC inhibitors. The term "therapeutically effective amount" means that sufficient compound is given to a patient to slow or halt the rate of tumor growth or cause a reduction in tumor volume. A therapeutically effective amount may also be evidenced by cells assuming a more differentiated phenotype, which may be manifested paradoxically and temporarily as an increase in tumor volume. In general, it is expected that a patient will be administered a daily dose of 1-2000 mg of HDAC inhibitor, preferably a daily dose of 10-1000 mg, and more preferably 50-600 mg. The cancers containing NUT rearrangements will typically be carcinomas of the aerodigestive tract or mediastinum, especially cancers of the trachea; pharynx; thymus; nasal cavity; thorax; sinuses; or larynx. However, cancers with NUT rearrangement also occur less frequently in other locations, such as bladder and bone.

The invention also encompasses methods of treating a patient for a solid tumor in which cells from the tumor are first assayed to determine whether they carry a NUT chromosomal rearrangement. If this assay indicates that the chromosomal rearrangement is present, the patient is administered a therapeutically effective amount of compound that promotes increased acetylation of histones. Although any assay, including immunohisto-chemistry demonstrating NUT expression, may be used to determine whether cells carry a NUT rearrangement, the preferred assay is a fluorescence in situ hybridization (FISH) assay or conventional cytogenetics. As discussed above, histone deacetylase (HDAC) inhibitors, e.g., SAHA, FK-228, LBH-589, CRA-024781, and MS275 are the most preferred therapeutic compounds but other compounds promoting increased acetylation may also be used. Preferred dosages and types of cancers most typically treated are given above.

In another aspect, the invention encompasses methods of determining whether cancer cells will respond to a histone deacetylase inhibitor by performing an assay (preferably a FISH assay) to determine if the cells have a NUT chromosomal rearrangement or express NUT or a NUT-fusion protein.

The invention encompasses multiwell assay plates containing serial dilutions of at least one, and preferably 5 or more, histone deacetylase (HDAC) inhibitors (or compounds being tested for NMC activity), each well having only one species of compound. Examples of compounds that may be bound to wells include: CRA-024781; APHA; bortezomib; Apicidin, CI-994; FK228; HC-Toxin; ITF2357; LAQ824; LBH589; MGCD0103; MS275; Niltubacin; Oxamflatin; PXD101; Pyroxamide; SAHA; Scriptaid; TSA; Tubacin; Nialamide; PBA; PBHA; Phenylzine; Tranylcypromine; VPA; and VPHA. Preferred compounds are CRA-024781, SAHA, FK-228, LBH-589 and MS275. The plates may be used for testing the responsiveness of NMC cells to treatment by each of the bound compounds. This may be accomplished by: a) incubating test NMC cells in the wells of the multiwell assay plate; b) assaying the test cells in each well to determine proliferation; histone acetylation; and/or expression of a protein (such as keratin) characteristic of cells that have become differentiated; and c) concluding that the NMC cells are responsive to the compound present in an assay well if the assay of step b) indicates that, relative to control NMC cells incubated under the same conditions but in the absence of compound, the test NMC cells exhibit reduced proliferation, increased histone acetylation and/or increased expression of a protein that identifies cells that have become differentiated. In a preferred embodiment, the cells are analyzed using antibody that recognizes acetylated histones or keratin.

DETAILED DESCRIPTION OF THE INVENTION

NUT midline carcinoma (NMC) is a rare, highly lethal cancer that occurs in children and adults of all ages. NMCs occur in the midline, most commonly in the head, neck, or mediastinum, as poorly differentiated carcinomas with variable degrees of squamous differentiation. This tumor is defined by rearrangement of the "nuclear protein in testis" (NUT) gene on chromosome 15q14. In most cases, NUT is involved in a balanced translocation with the BRD4 gene on chromosome 19p13.1, an event that creates a BRD4-NUT fusion gene. Variant rearrangements, some involving the BRD3 gene, occur in the remaining cases. NMC may be diagnosed by detection of NUT rearrangement by fluorescence in situ hybridization, karyotype analysis, or RT-PCR. Due its rarity and lack of characteristic histologic features, most cases of NMC currently go unrecognized.

NMC Defined Molecularly

NMC is defined herein as any malignant epithelial tumor with rearrangement of the NUT gene. In approximately ⅔ of cases, NUT (chromosome 15q14) is fused to BRD4, on chromosome 19p13.1, forming the BRD4-NUT fusion gene. In the remaining ⅓ of cases, the partner gene is BRD3 or other uncharacterized gene. We term these NUT-variant fusion genes. The histologic features of NMC are not distinctive, and diagnosis is based on detection of the NUT rearrangement. NUT rearrangements define NMCs, and for this reason the diagnosis is never in question once rearrangement of NUT has been demonstrated.

Diagnosis

As noted above, normal NUT expression is restricted almost exclusively to the testis. Thus, positive nuclear immunohistochemical (IHC) staining for NUT in tissues outside the testis is indicative of aberrant expression, such as in NMCs, where both BRD4-NUT and NUT-variants localize to the nucleus. Testing of rabbit polyclonal NUT antibodies for diagnostic utility using a panel of five NMCs and twenty-three NUT-unrelated poorly differentiation carcinomas of the upper aerodigestive tract suggests a specificity of 95% and a sensitivity of 60%. This may be somewhat less sensitive than one would like in a diagnostic test that is envisioned as a screen for the selection of tumors for confirmatory FISH testing. However, NUT monoclonal antibodies may permit the development of a more sensitive, IHC-based diagnostic screening test.

Assays for Chromosomal Rearrangements

In order to carry out assays to determine whether a NUT rearrangement has occurred in a cancer, tumor cells must first be obtained, e.g., by fine needle aspiration or a tissue biopsy. Any assay may then be used to determine whether cells are present having a rearrangement of the type discussed above. For example, the polymerase chain reaction may be used to amplify sequences in regions that would indicate that a fusion has occurred (Engleson, et al. *BMC Cancer* 6:69 (2006), incorporated herein by reference in its entirety). The preferred assay is the fluorescence in situ hybridization (FISH) assay described in French et al., *Am. J. Pathol.* 159:1987-1992 (2001) and French et al., *Oncogene* 27 (15):2237-2242 (Apr. 3, 2007), incorporated herein by reference in their entirety. This dual color, split-apart assay is performed on frozen tissue, air-dried cells, methanol-acetic acid preparation of metaphase-arrested cells, formalin-fixed, paraffin-embedded, unstained, 4-µm sections of tumor, or formalin-fixed, paraffin-embedded, unstained disaggregated thick (50 um) sections of tumor. Probes used for the BRD4 breakpoint on chromosome 19p13.1 break point included telomeric bacterial artificial chromosome (BAC) clone 87m17 (green) and centromeric yeast artificial chromosome (YAC) clone 766e7 (red). Presently, telomeric tandem BACs, RP11-319o10 and RP11-681d10, and centromeric tandem BACs, RP11-207i16 and CTD-3055m5 are used to assay for the BRD4 breakpoint. Probes used for the 15q13 break point (NUT), flanking a 181-kb region, include telomeric BAC clones 1H8 and 64o3 (green) and centromeric clones 412e10 (recently replaced with 1084a12) and 3d4 (red). Probes used for the BRD3 (chromosome 9q34.2) include telomeric BAC clone 145e17 (green), and centromeric BAC clone 2243h5 (red).

HDAC Inhibitors

Treatment methods described herein include the use of HDAC inhibitors. These compounds have been very extensively studied in the treatment of several diseases, including various types of cancer. As a result, a very large number of inhibitors have been developed and some are commercially available. Compounds that may be used in connection with the present invention are described in: U.S. Pat. Nos. 7,381,825; 7,381,749; 7,375,228; 7,375,137; 7,368,572; 7,345,043; 7,312,247; 7,291,492; 7,288,567; 7,282,608; RE39,850; 7,271,195; 7,265,154; 7,253,204; 7,250,514; 7,250,504; 7,244,751; 7,214,831; 7,205,304; 7,193,105; 7,169,801; 7,154,002; 7,135,493; 7,091,229; 7,057,057; 6,905,669; 6,897,220; 6,673,587; 6,638,530; 6,541,661; 6,495,719; 20080146623; 20080139547; 20080139535; 20080132503; 20080132459; 20080112889; 20080108601; 20080096920; 20080039509; 20080033015; 20080015216; 20080015190; 20070293530; 20070292351; 20070281934; 20070213330; 20070149495; 20070142393; 20070135438; 20070135431; 20070135424; 20070122507; 20070105808; 20070037869; 20060264415; 20060235231; 20060199829; 20060167103; 20060148743; 20060106049; 20060052599; 20060047123; 20060030554; 20060030543; 20060020131; and 20050288282. All of these references are hereby incorporated by reference in their entirety.

Pharmaceutical Compositions

The therapeutic compounds described herein may be incorporated into pharmaceutical compositions in accordance with methods that are standard in the art (see e.g., *Remington's Pharmaceutical Sciences*, Mack Publishing Co., (1990)). Formulations may be designed for delivery by any of the routes commonly used in the art.

Therapeutic compounds may be used in conjunction with any of the vehicles and excipients commonly employed in pharmaceutical preparations including water, salt solutions, alcohols, gum arabic, vegetable oils, benzo-alcohols, polyethylene glycol, gelatin, carbohydrates such as lactose, amylase, or starch; magnesium stearate; talc; salycic acid; paraffin; fatty acid esters; polymers; etc. The pharmaceutical preparations can be sterilized and, if desired, mixed with auxiliary agents such as: dispersants; lubricants; preservatives; stabilizers; wetting agents; emulsifiers; salts for influencing osmotic pressure; buffers; coloring agents; flavoring agents; and/or aromatic substances.

Solutions, particularly solutions for injection, can be prepared using water or physiologically compatible organic solvents such ethanol, 1,2-propylene glycol; polyethylene glycol; polygycols; dimethylsulfoxides; fatty alcohols; triglycerides; partial esters of glycerine; and the like. The preparations can be made using conventional techniques and may include sterile isotonic saline, water, 1,3-butanediol, ethanol, 1,2-propylene glycol, polygycols mixed with water, ringers Ringer's solution etc.

Dosage Forms and Routes of Administration

The present invention is compatible with any route of administration including oral, peroral, internal, rectal, nasal, lingual, transdermal, intravenous, intraarterial, intramuscular, intraperitoneal, intracutaneus, and subtaneous routes. Dosage forms that may be used include tablets, capsules, powders, aerosols, suppositories, skin patches, parenterals, sustained release preparations and oral liquids, including suspensions solutions and emulsions. The most preferred routes for administration are oral, by injection, or by infusion.

If desired, compositions, particularly compositions for injection, may be freeze-dried and lyophilizates reconstituted before administration. Dosage forms may include compounds promoting an increase in histone acetylation as the sole active ingredient or may include other active agents as well. All dosage forms may be prepared using methods that are standard in the art and that are taught in reference works such as *Remington's Pharmaceutical Sciences* (Osol, A, ed., Mack Publishing Co. (1990)).

EXAMPLES

The results obtained from experiments, and conclusions drawn based on the results, may be summarized as follows:

A. Association of BRD-NUT with Decreased Acetylation and Transcription

Expression profiling was performed using two NMC cell lines, TC-797 (Toretsky, et al., *Am. J. Clin. Oncol.* 26(3):300-306 (2003)) and PER-403 (Kees, et al., *Am. J. Ped. Hematol./Oncol.* 13(4):459-464 (1991)) treated with control or NUT siRNA. Twenty-four hours following knockdown of BRD4-NUT in the two NMC cell lines, prior to the phenotypic features of differentiation, the number of upregulated genes was found to vastly outnumber the number of genes that are downregulated, as quantified on whole-genome expression array chips (Affymetrix HGU-133 plus 2.0).

Immunoblots of the NMC cell lines TC-797 and PER-403 (Kuzume, et al., *Intn'l J. Cancer* 50(2):259-264 (1992)) treated with NUT siRNA or control siRNA revealed a global increase in acetylated histone H4, H3K18, and H4K8 in response to NUT siRNA. Consistent with this was a finding that 293T cells containing a Tet-inducible BRD4-NUT construct showed globally reduced staining for the same acetyl-histone marks in response to BRD4-NUT induction.

Consistent with a role in transcriptional repression, BRD4-NUT exhibits dominant-negative activity on a BRD4 transcriptional target, an HIV LTR-driven luciferase reporter gene.

B. Reversing BRD-NUT-Induced Chromatin Remodeling

Immunostaining experiments were performed to compare the spatial distribution of acetylated chromatin with that of BRD4-NUT in situ. It was found that acetylated chromatin, in the absence of BRD4-NUT, is diffusely distributed throughout the nucleus. In contrast, in the presence of BRD4-NUT, acetylation marks become speckled and co-localize with BRD4-NUT.

C. HDAC Inhibition in NMC

Studies aimed at testing the hypothesis of HDAC inhibitor therapy in NMC have been conducted using trichostatin A (TSA), and vorinostat (SAHA, Zolinza®). Both of these compounds are regarded as non-selective for class I and II deacetylases and bind HDAC proteins by chelating the active site zinc atom with a hydroxamic acid feature. NMC cells cultured in vitro were treated with TSA in dose- and time-ranging studies. Using immunofluorescence microscopy, it was found that there was an increase in histone acetylation with increasing dose and time of exposure. Interestingly, a redistribution of both BRD-NUT and acetylation marks from nuclear speckles to a diffuse pattern was also observed. With further drug exposure, a differentiation phenotype was observed by bright-field microscopy and by immunohistochemistry for the epithelial differentiation-associated protein, keratin. Within 24 hours following TSA (25 nM), NMC cell lines rapidly differentiate, as assessed by brightfield microscopy, in a manner similar to that seen when BRD-NUT is inhibited with specific siRNAs. Specifically, TSA caused changes in cellular morphology and increases in cytoplasmic keratin staining that are consistent with squamous differentiation.

These findings suggest that TSA treatment phenocopies direct interference with BRD-NUT. Consistent with an effect of TSA due to HDAC inhibition, rather than off-target effects or secondary toxicities, treatment of five NMC cell lines with pharmacologic doses of suberoylanilide hydroxamic acid (SAHA), an FDA-approved HDAC inhibitor with a spectrum of activities similar to that of TSA (class I and HDAC6 inhibition), also resulted in differentiation and arrested growth.

D. Assembly of Chemical Library of HDAC Inhibitors

In order to explore the response of NMC cells to HDAC inhibitors, we assembled a library of compounds shown in Table 1. Compounds were either purchased commercially or chemically synthesized and plated in serial dilutions (384 wells) with appropriate numbers of control, and solvent-only wells.

TABLE 1

Pharma HDAC Inhibitor Library

| Name | Chemotype |
| --- | --- |
| APHA | Hydroxamic acid |
| Apicidin | Ketone |
| CI-994 | Hydroxamic acid |
| CRA-024781 | Hydroxamic acid |
| FK228 | Thiol |
| HC-Toxin | Epoxide |
| ITF2357 | Hydroxamic acid |
| LAQ824 | Hydroxamic acid |
| LBH589 | Hydroxamic acid |
| MGCD0103 | Benzamide |
| MS275 | Benzamide |
| Niltubacin | Carboxylic acid |
| Oxamflatin | Hydroxamic acid |
| PXD101 | Hydroxamic acid |
| Pyroxamide | Hydroxamic acid |
| SAHA | Hydroxamic acid |
| Scriptaid | Hydroxamic acid |
| TSA | Hydroxamic acid |
| Tubacin | Hydroxamic acid |
| Nialamide | MAOI |
| PBA | Carboxylic acid |
| PBHA | Hydroxamic acid |
| Phenylzine | MAOI |
| Tranylcypromine | MAOI |
| VPA | Carboxylic acid |
| VPHA | Hydroxamic acid |

E. Development of High-Throughput, High-Content Assays

A cell based approach was developed for identifying potent and selective HDAC inhibitors. Nuclear acetylation correlates with inhibition of class I deacetylases such as HDAC1 and HDAC2. An automated epiflourescent assay was therefore developed which is measures histone hyperacetylation. Cells were seeded in 384-well plate format (500 cells/well) and treated with compound. They were then fixed and stained with: a) Hoechst (nuclei); b) primary anti-AcHistone polyclonal Ab; c) anti-Keratin monoclonal antibody; and d) compatible flurophore-conjugated secondary antibodies. After automated image acquisition, a custom analysis program was applied that identifies and masks cells based on nuclear intensity (Hoechst) and then derives quantitative fluorescent data from the FITC (AcHistone) image. Subsequent secondary masks were generated using cytosolic intensity.

F. Adaptation of the Screening Assay (HCS) to NMC Culture.

We have performed studies of HDAC inhibitor effects on NMC cells in culture using an adaptation of the assay described above. In studies of the effect of SAHA on NMC (TC797) cells in a 384-well plate format, we have observed increased histone acetylation qualitatively in images derived from dose-ranging experiments. In a first attempt at multiplexed detection and quantification of effects on cell proliferation, histone acetylation, and keratin protein expression, we have witnessed clear, dose-response activity of SAHA in the pharmacologically achievable range ($C_{max}$ approximately 2 µM). It was found that SAHA caused a reduction in cell proliferation and an induction of increased keratin protein content that correlated with an increase in histone acetylation ($R^2=0.99$).

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of treating a NUT chromosomal rearrangement cancer in a patient diagnosed with said NUT chromosomal rearrangement cancer, wherein said cancer comprises a fusion between the NUT (nuclear protein in testis) gene and a bromo domain gene selected from BRD3 and BRD4, said method comprising administering to said patient a therapeutically effective amount of a histone deacetylase (HDAC) inhibitor.

2. The method of claim 1, wherein said HDAC inhibitor is selected from the group consisting of: is suberoyl anilide hydroxamic acid (SAHA); CRA-024781; romidepsin (FK-228); LBH-589 and MS275.

3. The method of claim 1, wherein said HDAC inhibitor is suberoyl anilide hydroxamic acid (SAHA).

4. The method of claim 1, wherein said HDAC inhibitor is administered to said patient at a daily dose of 10-1000 mg.

5. The method of claim 1, wherein said HDAC inhibitor is administered to said patient at a daily dose of 50-600 mg.

6. The method of claim 1, wherein said cancer is a carcinoma of the aerodigestive tract or mediastinum of said patient.

7. The method of claim 1, wherein said cancer is a carcinoma of the nasopharynx; orbit; trachea; pharynx; thymus; posterior mediastinum; nasal cavity; thorax; sinuses; larynx; or bronchi.

8. The method of claim 1, wherein said cancer is a carcinoma of the bladder or salivary gland.

9. The method of claim 1, wherein:
   a) said cancer is a carcinoma of the nasopharynx; orbit; trachea; pharynx; thymus; posterior mediastinum; nasal cavity; thorax; sinuses; larynx; or bronchi;
   b) said HDAC inhibitor is administered to said patient at a daily dose of 10-1000 mg and is selected from the group consisting of said HDAC inhibitor is selected from the group consisting of: CRA-024781; romidepsin (FK-228); LBH-589; MS275 and SAHA.

10. The method of claim 9, wherein said HDAC inhibitor is administered to said patient at a daily dose of 50-600 mg.

11. The method of claim 9, wherein said HDAC inhibitor is SAHA.

12. The method of claim 9, wherein said cancer is a carcinoma of the nasopharynx, orbit, or trachea.

13. The method of claim 9, wherein said cancer is a carcinoma of the pharynx.

14. The method of claim 9, wherein said cancer is a carcinoma of the thymus.

15. The method of claim 9, wherein said cancer is a carcinoma of the posterior mediastinum.

16. The method of claim 9, wherein said cancer is a carcinoma of the nasal cavity.

17. The method of claim 9, wherein said cancer is a carcinoma of the thorax.

18. The method of claim 9, wherein said cancer is a carcinoma of the sinuses.

19. The method of claim 9, wherein said cancer is a carcinoma of the larynx.

20. The method of claim 9, wherein said cancer is a carcinoma of the bronchi.

\* \* \* \* \*